United States Patent
Marcotulli et al.

(10) Patent No.: US 12,109,206 B2
(45) Date of Patent: *Oct. 8, 2024

(54) NICOTINAMIDE RIBOSIDE AND PTEROSTILBENE COMPOSITIONS AND METHODS FOR TREATMENT OF SKIN DISORDERS

(71) Applicant: Elysium Health, Inc., New York, NY (US)

(72) Inventors: Eric A. Marcotulli, New York, NY (US); Daniel A. Alminana, New York, NY (US); Paul M. Bowen, Newton, MA (US)

(73) Assignee: Elysium Health, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/872,575

(22) Filed: Jul. 25, 2022

(65) Prior Publication Data
US 2022/0362233 A1     Nov. 17, 2022

Related U.S. Application Data

(63) Continuation of application No. 15/735,066, filed as application No. PCT/US2016/019653 on Feb. 25, 2016, now Pat. No. 11,426,398.

(60) Provisional application No. 62/173,733, filed on Jun. 10, 2015.

(51) Int. Cl.
| | |
|---|---|
| A61K 8/368 | (2006.01) |
| A61K 8/67 | (2006.01) |
| A61K 9/00 | (2006.01) |
| A61K 9/48 | (2006.01) |
| A61K 31/09 | (2006.01) |
| A61K 31/455 | (2006.01) |
| A61K 31/706 | (2006.01) |
| A61P 17/00 | (2006.01) |
| A61Q 19/00 | (2006.01) |

(52) U.S. Cl.
CPC ............ *A61K 31/455* (2013.01); *A61K 8/368* (2013.01); *A61K 8/675* (2013.01); *A61K 9/0053* (2013.01); *A61K 9/4866* (2013.01); *A61K 31/09* (2013.01); *A61K 31/706* (2013.01); *A61P 17/00* (2018.01); *A61Q 19/004* (2013.01); *A61K 2300/00* (2013.01)

(58) Field of Classification Search
CPC ...... A61K 31/455; A61K 8/368; A61K 8/675; A61K 9/0053; A61K 9/4866; A61K 31/09; A61K 31/706; A61P 17/00; A61Q 19/004

See application file for complete search history.

(56) References Cited

U.S. PATENT DOCUMENTS

| | | |
|---|---|---|
| 8,106,184 B2 | 1/2012 | Sauve et al. |
| 11,426,398 B2 | 8/2022 | Marcotulli et al. |
| 2012/0172584 A1 | 7/2012 | Sauve et al. |
| 2012/0289605 A1 | 11/2012 | Bartos et al. |
| 2013/0136778 A1 | 5/2013 | Estrela Ariquel et al. |
| 2013/0296440 A1 | 11/2013 | Bartos |
| 2015/0011650 A1 | 1/2015 | Bartos et al. |

FOREIGN PATENT DOCUMENTS

| | | |
|---|---|---|
| CN | 102639126 A | 8/2012 |
| CN | 103547256 A | 1/2014 |
| EP | 2322159 A1 | 5/2011 |
| JP | 2013509385 A | 3/2013 |
| WO | WO-2011/051483 A1 | 5/2011 |
| WO | WO-2013/169291 A2 | 11/2013 |
| WO | WO-2015/066382 A1 | 5/2015 |
| WO | WO-2015/186114 A1 | 12/2015 |
| WO | WO-2016/149277 A1 | 9/2016 |
| WO | WO-2016/149395 A1 | 9/2016 |
| WO | WO-2016/200447 A1 | 12/2016 |

OTHER PUBLICATIONS

Chen et al., "A Phase 3 Randomized Trial of Nicotinamide for Skin-Cancer Chemoprevention," New England Journal of Medicine, 373(17):1618-1626 (2015).
Chen et al., "Oral and systemic photoprotection," Photodermatology, photoimmunology & photomedicine, 30(2-3): 102-111 (2014).
Estrela et al., "Pterostilbene: Biomedical applications," Crit Revs Clin Lab Sci 50(3):65-78 (2013).
Extended European Search Report for EP Application No. 16807948.8 mailed Feb. 25, 2019.
International Search Report and Written Opinion for International Application No. PCT/US2016/019653 dated May 2, 2016.
Yiasemides et al., "Oral nicotinamide protects against ultraviolet radiation-induced immunosuppression in humans," Carcinogenesis, 30(1): 101-105 (2009).

*Primary Examiner* — Abigail Vanhorn

(74) *Attorney, Agent, or Firm* — Foley Hoag LLP; Brendan T. Jones; Allison L. Gilder

(57) ABSTRACT

Compositions containing a combination of nicotinamide riboside and pterostilbene for treating skin disorders, and methods of treating skin disorders using these compositions and their equivalents are described. The skin disorders that are treated using these compositions or methods include sun exposure-related skin disorders, inflammatory skin disorders, autoimmune disease-related skin disorders and cancer-related skin disorders. In one embodiment, the compositions containing a combination of nicotinamide riboside and pterostilbene are prepared as oral formulations.

6 Claims, No Drawings

NICOTINAMIDE RIBOSIDE AND PTEROSTILBENE COMPOSITIONS AND METHODS FOR TREATMENT OF SKIN DISORDERS

REFERENCE TO RELATED APPLICATION

This application is a continuation of U.S. application Ser. No. 15/735,066, filed Dec. 8, 2017, which is a § 371 national-stage application based on PCT Application PCT/US16/019653, filed Feb. 25, 2016, which claims the benefit of U.S. Provisional Application No. 62/173,733, filed Jun. 10, 2015, which is incorporated herein by reference in its entirety.

FIELD OF THE INVENTION

The field of the invention generally relates to compositions and methods for the treatment of skin disorders. In particular, the invention relates to nicotinamide riboside and pterostilbene compositions and methods for treatment of skin disorders.

BACKGROUND OF THE INVENTION

Skin disorders are amongst the most common human ailments. They affect between about 30% and about 70% of individuals, and rank as the fourth leading cause of nonfatal disease burden at the global level. (Hay, et al., J. Invest. Dermatol. 2014, 134, 1527-1534). According to the most recent studies by the International Classification of Disease, 10 classifications of human diseases, there are more than a thousand skin disorders, with a few conditions accounting for the majority of skin disease burden (Hay, et al., J. Invest. Dermatol. 2014, 134, 1527-1534). Collectively, skin disorders were the fourth leading cause of nonfatal burden expressed as years lost due to disability in 2010. Skin disorders cause several detrimental effects on individuals, such as impair health-related quality of life, fear of negative evaluation by others, physical incapacity and death. Nonetheless, skin disorders continue to receive very little attention (Hay, et al., J. Invest. Dermatol. 2014, 134, 1527-1534).

Standard treatments include avoidance of triggers such as sun exposure. Compositions of therapeutic or prophylactic agents can be delivered systemically, such as via oral administration, applied topically or injected into the dermis layer. A variety of treatments and methods have been used over the years including the topical application of corticosteroids; vitamin D3 analogs such as calcipotriene; coal tar, etc. Bath solutions and general moisturizers have been utilized by some patients. Sunlight and ultraviolet light treatments have also been used. Systemic treatment with retinoids, methotrexate, cyclosporine, hydroxyurea and antibiotics is sometimes required. More recently, new biologic agents and biologic-immune-response modifiers such as alefacept, efalizumab, and etanercept have been developed.

Each of these treatments has its benefits and drawbacks. In many instances, patients develop a tolerance to the treatment resulting in decreased effectiveness. In addition, these treatments are often messy, have an unpleasant odor, and are repetitive and tedious for patients.

U.S. Pat. No. 9,00,147 to Suave, et al., describes oral and topical compositions of nicotinoyl ribosides and nicotinamide riboside derivatives for treating skin disorders. European Patent No. 2,493,462 describes compositions containing pterostilbene and optionally quercetin or any acceptable salts thereof, for use in the prevention, treatment, or both, of skin diseases and injuries via topical administration. WO 2015/066382 describes oral and topical skin care compositions containing nicotinamide riboside, or its salts, optionally in combination with a compound such as stilbenoids (e.g., pterostilbene), curcumin, peptides, retinols, salicylic acid, benzoyl peroxide, vitamin C (L-ascorbic acid), anthocyanins, or combinations thereof.

In view of the many detrimental effects and the little attention paid to skin disorders, there is a need for formulations and methods for the systemic treatment of skin disorders that does not involve antibiotics and immunosuppressants.

DETAILED DESCRIPTION OF THE INVENTION

A composition comprising a combination of a therapeutically effective amount of nicotinamide riboside and a therapeutically effective amount of pterostilbene; and a pharmaceutically acceptable excipient, wherein the combination is in a therapeutically effective amount for treatment of a skin disorder.

A method comprising administering a combination of a therapeutically effective amount of nicotinamide riboside and a therapeutically effective amount of pterostilbene for treatment of a skin disorder in a patient in need of treatment thereof.

Oral formulations and methods of treating skin disorders are described. In certain embodiments, a composition may contain a therapeutically effective amount of nicotinamide riboside, a therapeutically effective amount of pterostilbene, or both. In certain embodiments, a composition may contain nicotinamide riboside and pterostilbene. In certain embodiments, a method may include administering a therapeutically effective amount of nicotinamide riboside and/or pterostilbene. In certain embodiments, a method may include orally administering a therapeutically effective amount of a combination of nicotinamide riboside and pterostilbene. In certain embodiments, a method may include orally administering a therapeutically effective amount of a combination of nicotinamide riboside and pterostilbene to treat a skin disorder.

In certain embodiments, a composition may contain a therapeutically effective amount of nicotinamide riboside, a therapeutically effective amount of pterostilbene, or both. In certain embodiments, a composition may contain nicotinamide riboside and pterostilbene. In certain embodiments, a method may include administering a therapeutically effective amount of nicotinamide riboside and/or pterostilbene. In certain embodiments, a method may include topically administering a therapeutically effective amount of a combination of nicotinamide riboside and pterostilbene. In certain embodiments, a method may include topically administering a therapeutically effective amount of a combination of nicotinamide riboside and pterostilbene to treat a skin disorder.

In certain embodiments, nicotinamide riboside may be administered in an amount of between about 100 mg and about 1000 mg per day. Nicotinamide riboside may be administered in combination with pterostilbene that may be administered in an amount of between about 25 mg and about 500 mg per day.

In certain embodiments, nicotinamide riboside may be administered in an amount of between about 200 mg and about 700 mg per day. Nicotinamide riboside may be administered in combination with pterostilbene that may be administered in an amount of between about 25 mg and about 250 mg per day.

In certain embodiments, nicotinamide riboside may be administered in an amount of about 250 mg per day. Nicotinamide riboside may be administered in combination with pterostilbene that may be administered in an amount of between about 25 mg and about 250 mg per day. In certain embodiments, nicotinamide riboside may be administered in an amount of about 250 mg per day. Nicotinamide riboside may be administered in combination with pterostilbene that may be administered in an amount of about 50 mg per day.

A composition comprising a combination of a therapeutically effective amount of nicotinamide mononucleotide and a therapeutically effective amount of epsilon-viniferin; and a pharmaceutically acceptable excipient, wherein the combination is in a therapeutically effective amount for treatment of a skin disorder.

A method comprising administering a combination of a therapeutically effective amount of nicotinamide mononucleotide and a therapeutically effective amount of epsilon-viniferin for treatment of a skin disorder in a patient in need of treatment thereof.

A composition comprising a combination of a therapeutically effective amount of nicotinamide mononucleotide and a therapeutically effective amount of niacin; and a pharmaceutically acceptable excipient, wherein the combination is in a therapeutically effective amount for treatment of a skin disorder.

A method comprising administering a combination of a therapeutically effective amount of nicotinamide mononucleotide and a therapeutically effective amount of niacin for treatment of a skin disorder in a patient in need of treatment thereof.

A composition comprising a combination of a therapeutically effective amount of nicotinamide riboside and a therapeutically effective amount of epsilon-viniferin; and a pharmaceutically acceptable excipient, wherein the combination is in a therapeutically effective amount for treatment of a skin disorder.

A method comprising administering a combination of a therapeutically effective amount of nicotinamide riboside and a therapeutically effective amount of epsilon-viniferin for treatment of a skin disorder in a patient in need of treatment thereof.

A composition comprising a combination of a therapeutically effective amount of nicotinamide riboside and a therapeutically effective amount of resveratrol; and a pharmaceutically acceptable excipient, wherein the combination is in a therapeutically effective amount for treatment of a skin disorder.

A method comprising administering a combination of a therapeutically effective amount of nicotinamide riboside and a therapeutically effective amount of resveratrol for treatment of a skin disorder in a patient in need of treatment thereof.

Pharmaceutical compositions containing nicotinamide ribose, pterostilbene or a combination thereof for treating skin disorders are described herein. In certain embodiments, the composition may contain a therapeutically effective amount of nicotinamide ribose. In certain embodiments, the composition may contain a therapeutically effective amount of pterostilbene.

In certain embodiments, the composition may contain a therapeutically effective amount of a combination of nicotinamide ribose and pterostilbene. The pharmaceutical composition can be in the form of a soft gel capsule or hard shell capsule, or other solid form such as a tablet. In certain embodiments, the pharmaceutical composition may contain about 250 mg of nicotinamide riboside and about 50 mg of pterostilbene. The pharmaceutical composition can be administered one or more times daily. In certain embodiments, the composition may be administered twice daily. In embodiments where the pharmaceutical composition is administered twice daily, the composition may contain about 125 mg of nicotinamide riboside and about 25 mg of pterostilbene. In certain embodiments, the compounds, compositions or pharmaceutical compositions containing nicotinamide riboside and pterostilbene may be prepared as oral formulations. In certain embodiments, the compounds, compositions or pharmaceutical compositions containing nicotinamide riboside and pterostilbene may be prepared as topical formulations.

Additional features, advantages, and embodiments of the invention are set forth or apparent from consideration of the following detailed description and claims. Moreover, it is to be understood that both the foregoing summary of the invention and the following detailed description are exemplary and intended to provide further explanation without limiting the scope of the invention as claimed.

I. Definitions

The terms "patient", "subject", "individual" or "host" refer to either a human or a non-human animal.

The terms "treating" and "improving" mean that a visual indicia of a skin disorder is cured, lessened, reduced, improved, ameliorated, palliated, prevented, and/or reversed after administration. Visual indicia of a skin disorder may be flushing, erythema, papules, pustules, telangiectasia, facial edema, rhinophyma, psoriasis, blushing, smoothness, roughness, hypervascularity, and/or facial blemishes.

As used herein, the term "therapeutically effective" refers to the amount of nicotinamide riboside and pterostilbene needed to produce a desired therapeutic result. In certain embodiments, nicotinamide mononucleotide, niacinamide, nicotinamide, nicotinic acid and/or niacin may be substituted for nicotinamide riboside. In certain embodiments, a combination of nicotinamide riboside, nicotinamide mononucleotide, and/or niacin may be used. In certain embodiments epsilon-viniferin and/or resveratrol may be substituted for pterostilbene. In certain embodiments, a combination of pterostilbene, epsilon-viniferin, and/or resveratrol may be used.

As used herein, the term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Stereoisomer", as used herein, refers to isomeric molecules that have the same molecular formula and sequence of bonded atoms (constitution), but which differ in the three dimensional orientations of their atoms in space. Examples of stereoisomers include enantiomers and diastereomers. As used herein, an enantiomer refers to one of the two mirror-image forms of an optically active or chiral molecule. A racemic mixture contains both forms of the optically active or chiral molecule. Diastereomers (or diastereoisomers) are stereoisomers that are not enantiomers (non-superimposable mirror images of each other). Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. A mixture of enantiomers can be enantiomerically enriched so that one enantiomer is present in an amount greater than 50%. Enantiomers and/or diasteromers can be resolved or separated using techniques known in the art.

"Substituted," as used herein, refers to all permissible substituents of the compounds or functional groups described herein. The permissible substituents can include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, which may be 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups. Such alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, poly(lactic-co-glycolic acid), peptide, and polypeptide groups can be further substituted.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl has 30 or fewer carbon atoms in its backbone (e.g., $C_1$-$C_{30}$ for straight chains, $C_3$-$C_{30}$ for branched chains), 20 or fewer, 15 or fewer, or 10 or fewer. Likewise, some cycloalkyls have from 3-10 carbon atoms in their ring structure, and may have have 5, 6 or 7 carbons in the ring structure. The term "alkyl" (or "lower alkyl") as used throughout the specification, examples, and claims can include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogens (such as fluorine, chlorine, bromine, or iodine), hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety, —NRR', wherein R and R' are independently hydrogen, alkyl, or aryl, and wherein the nitrogen atom is optionally quaternized; —SR, wherein R is hydrogen, alkyl, or aryl; —CN; —NO$_2$; —COOH; carboxylate; —COR, —COOR, or —CON(R)$_2$, wherein R is hydrogen, alkyl, or aryl; azide, aralkyl, alkoxyl, imino, phosphonate, phosphinate, silyl, ether, sulfonyl, sulfonamido, heterocyclyl, aromatic or heteroaromatic moieties, haloalkyl (such as —CF$_3$, —CH$_2$—CF$_3$, —CCl$_3$); —CN; —NCOCOCH$_2$CH$_2$, —NCOCOCHCH; —NCS; and combinations thereof.

Unless the number of carbons is otherwise specified, "lower alkyl" as used herein means an alkyl group, as defined above, but having from one to ten carbons, or one to six carbon atoms in its backbone structure. Likewise, "lower alkenyl" and "lower alkynyl" have similar chain lengths. Throughout the application, alkyl groups may be lower alkyls. In some embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Cycloalkyls can be substituted in the same manner.

The terms "alkenyl" and "alkynyl", refer to unsaturated aliphatic groups analogous in length and possible substitution to the alkyls described above, but that contain at least one double or triple bond respectively.

The term "substituted alkenyl" refers to alkenyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

The term "substituted alkynyl" refers to alkynyl moieties having one or more substituents replacing one or more hydrogen atoms on one or more carbons of the hydrocarbon backbone. Such substituents include, but are not limited to, halogen, azide, alkyl, aralkyl, alkenyl, alkynyl, cycloalkyl, hydroxyl, carbonyl (such as a carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, alkylthio, sulfate, sulfonate, sulfamoyl, sulfonamido, sulfonyl, heterocyclyl, alkylaryl, haloalkyl, —CN, aryl, heteroaryl, and combinations thereof.

"Aryl," as used herein, refers to $C_5$-$C_{26}$-membered aromatic, fused aromatic, fused heterocyclic, or biaromatic ring systems. "Aryl," as used herein, can include 5-, 6-, 7-, 8-, 9-, 10-, 14-, 18-, and 24-membered single-ring aromatic groups, for example, benzene, naphthalene, anthracene, phenanthrene, chrysene, pyrene, corannulene, coronene, etc. "Aryl" further encompasses polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles.

The term "substituted aryl" refers to an aryl group, wherein one or more hydrogen atoms on one or more aromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

"Heterocycle," "heterocyclic" and "heterocyclyl" are used interchangeably, and refer to a cyclic radical attached via a ring carbon or nitrogen atom of a monocyclic or bicyclic ring containing 3-10 ring atoms, and can have from 5-6 ring atoms, comprising carbon and one to four heteroatoms each selected from the group consisting of non-peroxide oxygen, sulfur, and N(Y) wherein Y is absent or is H, O, $C_1$-$C_{10}$ alkyl, phenyl or benzyl, and optionally containing 1-3 double bonds and optionally substituted with one or more substituents. Heterocyclyl are distinguished from heteroaryl by definition. Examples of heterocycles include, but are not limited to piperazinyl, piperidinyl, piperidonyl, 4-piperidonyl, dihydrofuro[2,3-b]tetrahydrofuran, morpholinyl, piperazinyl, piperidinyl, piperidonyl, 4-piperidonyl, piperonyl, pyranyl, 2H-pyrrolyl, 4H-quinolizinyl, quinuclidinyl, tetrahydrofuranyl, 6H-1,2,5-thiadiazinyl. Heterocyclic groups can optionally be substituted with one or more substituents as defined above for alkyl and aryl.

The term "heteroaryl" refers to $C_5$-$C_{26}$-membered aromatic, fused aromatic, biaromatic ring systems, or combinations thereof, in which one or more carbon atoms on one or more aromatic ring structures have been substituted with a heteroatom. Suitable heteroatoms include, but are not limited to, oxygen, sulfur, and nitrogen. Broadly defined, "heteroaryl," as used herein, includes 5-, 6-, 7-, 8-, 9-, 10-, 14-, 18-, and 24-membered single-ring aromatic groups that may include from one to four heteroatoms, for example, pyrrole, furan, thiophene, imidazole, oxazole, thiazole, triazole, tetrazole, pyrazole, pyridine, pyrazine, pyridazine and pyrimidine, and the like. The heteroaryl group may also be referred to as "aryl heterocycles" or "heteroaromatics". "Heteroaryl" further encompasses polycyclic ring systems having two or more rings in which two or more carbons are common to two adjoining rings (i.e., "fused rings") wherein at least one of the rings is heteroaromatic, e.g., the other cyclic ring or rings can be cycloalkyls, cycloalkenyls, cycloalkynyls, aryls, heterocycles, or combinations thereof. Examples of heteroaryl rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, purinyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, quinoxalinyl, tetrahydroisoquinolinyl, tetrahydroquinolinyl, tetrazolyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined below for "substituted heteroaryl".

The term "substituted heteroaryl" refers to a heteroaryl group in which one or more hydrogen atoms on one or more heteroaromatic rings are substituted with one or more substituents including, but not limited to, halogen, azide, alkyl, aralkyl, alkenyl, alkynyl, cycloalkyl, hydroxyl, alkoxy, carbonyl (such as a ketone, aldehyde, carboxyl, alkoxycarbonyl, formyl, or an acyl), silyl, ether, ester, thiocarbonyl (such as a thioester, a thioacetate, or a thioformate), alkoxyl, phosphoryl, phosphate, phosphonate, phosphinate, amino (or quarternized amino), amido, amidine, imine, cyano, nitro, azido, sulfhydryl, imino, alkylthio, sulfate, sulfonate, sulfamoyl, sulfonamido, sulfonyl, heterocyclyl, alkylaryl, haloalkyl (such as $CF_3$, —$CH_2$—$CF_3$, —$CCl_3$), —CN, aryl, heteroaryl, and combinations thereof.

The term "heteroatom" as used herein means an atom of any element other than carbon or hydrogen. Exemplary heteroatoms include nitrogen, oxygen and sulfur.

"Analog" and "Derivative" may be used interchangeably, and refer to a compound that possesses the same core as the parent compound, but differs from the parent compound in bond order, the absence or presence of one or more atoms and/or groups of atoms, and combinations thereof. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

II. Compositions

A. Active Agents
i. Nicotinamide Riboside

As discussed above, in certain embodiments, the methods and compositions contain nicotinamide riboside, a precursor of coenzyme $NAD^+$, which is involved in metabolic processes such as energy production, DNA repair, cellular detoxification, the inflammatory response, and protein folding. The chemical structure of nicotinamide riboside is provided below.

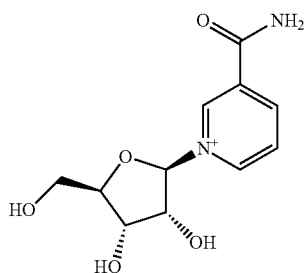

Formula I

Nicotinamide riboside has four asymmetric centers and that any optical isomer, as separated, pure or partially purified optical isomers and any mixtures thereof including racemic mixtures can be used. The enantiomeric form can be in enantiomeric excess, e.g., essentially in a pure form. Accordingly, some embodiments relate to nicotinamide riboside having an enantiomeric excess of at least 60%, at least 70%, at least 80%, at least 85%, at least 90%, at least 96%, at least 98%, and ranges therebetween.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography on an optically active matrix. The compounds of the present invention may also be resolved by the formation of diastereomeric derivatives. Additional methods for the resolution of optical isomers, known to those skilled in the art, may be used. Such methods include those discussed by J. Jacques, A. Collet and S. Wilen in "Enantiomers, Racemates, and Resolutions", John Wiley and Sons, New York (1981). Optically active compounds can also be prepared from optically active starting materials.

Nicotinamide riboside is a quaternary salt and forms an ionic bond with a counteranion. Examples of counteranions include the anions of suitable organic acid such as formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid counteranions include the pharmaceutically acceptable salts listed in J. Pharm. Sci. 66, 2 (1977)). In certain other embodiments, the active agent is a derivative, salt, solvate, or prodrug of nicotinamide riboside. In some embodiments, the ribose in nicotinamide riboside is (3-D-ribose. In certain embodiments, nicotinamide riboside may be substituted or combined with nicotinamide mononucleotide, niacinamide, nicotinamide, nicotinic acid, and/or niacin.

In some embodiments, the active agent has a chemical structure according to Formula I:

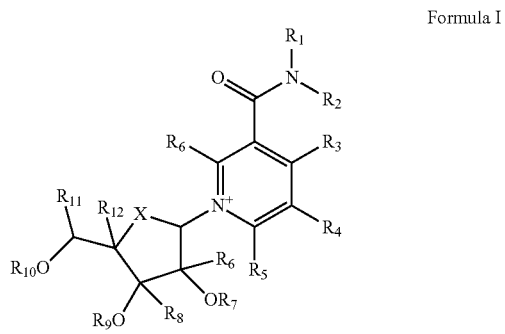

Formula I or is a pharmaceutically salt thereof, wherein:
X is O, S, or NR;
$R_1$ and $R_2$ may be hydrogen, a substituted or unsubstituted alkyl group, a substituted or unsubstituted alkenyl group, a substituted or unsubstituted alkynyl group, a substituted or unsubstituted non-aromatic heterocyclic group or a substituted or unsubstituted aryl group;
$R_3$, $R_4$, $R_5$, and $R_6$ may be selected from the group consisting of hydrogen, a substituted or unsubstituted alkyl group, a substituted or unsubstituted aryl group, a substituted or unsubstituted non-aromatic heterocyclic group, halogen. —OR, —CN, —$CO_2R$, —OCOR, —$OCO_2R$, —C(O)NRR', —OC(O)NRR', —C(O)R, —COR, —SR, —$OSO_3H$, —$S(O)_nR$, —$S(O)_nOR$, —$S(O)_nNRR'$, —NRR', —NRC(O)OR', —$NO_2$ and —NRC(O)R';
$R_7$, $R_9$, and $R_{10}$ may be selected from the group consisting of hydrogen, a substituted or unsubstituted alkyl group, a substituted or unsubstituted aryl group, —C(O)R, —C(O)OR, —C(O)NHR, —C(O)NRR', —$S(O)_nR$, —$S(O)_nOR$, —$S(O)_nNRR'$, —C(S)R, —C(S)OR and —C(O)SR; and
$R_8$, $R_{11}$, and $R_{12}$, may be selected from the group consisting of hydrogen, a substituted or unsubstituted alkyl group, a substituted or unsubstituted aryl group, a substituted or unsubstituted non-aromatic heterocyclic group, halogen, —CN, —$CO_2R$, —OCOR, —$OCO_2R$, —C(O)NRR', —OC(O)NRR', —C(O)R, —COR, —$OSO_3H$, —$S(O)_nR$, —$S(O)_nOR$, —$S(O)_nNRR'$, —NRR', —NRC(O)OR', —$NO_2$ and —NRC(O)R';
wherein R and R' may be hydrogen, a substituted or unsubstituted alkyl group, a substituted or unsubstituted aryl group or a substituted or unsubstituted non-aromatic heterocyclic group; and n is 1 or 2. Compounds of Formula I may include isomers, enantiomers, and stereoisomers thereof.

ii. Pterostilbene

Pterostilbene is a polyphenol based derivative of resveratrol and, like the NAD precursor, promotes metabolic health. The chemical structure of pterostilbene is provided below:

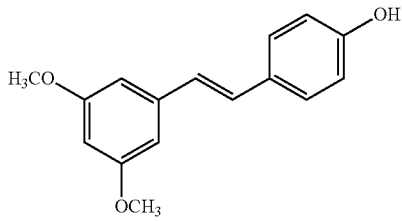 [SMILES: COc1cc(/C=C/c2ccc(O)cc2)cc(OC)c1]

In some embodiments, the active agent is a derivative, salt, solvate, or prodrug of pterostilbene. In certain embodiments, pterostilbene may be substituted and/or combined with epsilon-viniferin and/or resveratrol.

In certain other embodiments, the active agent is a stilbene having a chemical structure according to Formula II:

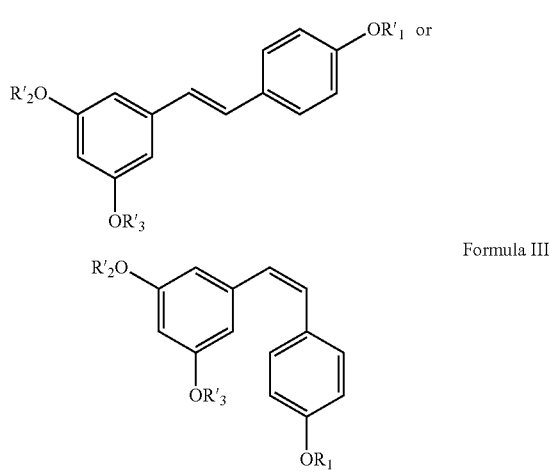

or is a pharmaceutically acceptable salt thereof, wherein:
$R'_1$, $R'_2$, and $R'_3$ may be hydrogen, a substituted or unsubstituted alkyl group, a substituted or unsubstituted aryl group, —C(O)R, —C(O)OR, —C(O)NHR, —C(O)NRR', —S(O)$_n$R, —S(O)$_n$OR, —S(O)$_n$NRR', —C(S)R, —C(S)OR and —C(O)SR;
wherein R and R' may be hydrogen, a substituted or unsubstituted alkyl group, a substituted or unsubstituted aryl group or a substituted or unsubstituted non-aromatic heterocyclic group; and n is 1 or 2. Compounds of Formula II and Formula III may include isomers, enantiomers, and stereoisomers thereof.

B. Routes of Administration

In one embodiment the compounds, compositions or pharmaceutical compositions are formulated for oral delivery, i.e., in an oral formulation. Oral solid dosage forms are described generally in Remington's Pharmaceutical Sciences, 18$^{th}$ Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc., or into liposomes. Such compositions may influence the physical state, stability, rate of in vivo release, and rate of in vivo clearance of the disclosed. See, e.g., Remington's Pharmaceutical Sciences, 18$^{th}$ Ed. (1990, Mack Publishing Co., Easton, Pa. 18042) pages 1435-1712. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013,556). See also, Marshall, K. In: Modern Pharmaceutics Edited by G. S. Banker and C. T. Rhodes Chapter 10, 1979. The formulation may include a peptide (or chemically modified forms thereof) and inert ingredients which protect compounds in the stomach environment, and release of the biologically active material in the intestine.

Nicotinamide riboside, niacinamide, nicotinamide, nicotinic acid, pterostilbene, nicotinamide mononucleotide, niacin, epsilon-viniferin, resveratrol or derivatives thereof may be chemically modified so that oral and/or topical delivery of the compound is efficacious. Contemplated chemical modification is the attachment of at least one moiety to the component molecule itself, where the moiety permits uptake into the blood stream from the stomach or intestine, or uptake directly into the intestinal mucosa. Also contemplated is the increase in overall stability of the component or components and increase in circulation time in the body. Certain embodiments may be pharmaceutical compositions. Certain embodiments may be nutritional supplements.

Certain embodiments provide liquid dosage forms for oral administration, including pharmaceutically acceptable emulsions, solutions, suspensions, and syrups, which may contain other components including inert diluents; adjuvants such as wetting agents, emulsifying and suspending agents; and sweetening, and flavoring agents.

Controlled release oral formulations may be provided. Controlled release may include, but is not limited to, delayed release and pH-dependent release. In certain embodiments, the nicotinamide riboside and pterostilbene, or derivatives thereof can be incorporated into microcapsules, microparticulates, nanoparticulates, etc. through use of coatings to affect release of the active principle. In certain embodiments, nicotinamide riboside and pterostilbene, or derivatives thereof can be incorporated into an inert matrix which permits release by either diffusion or leaching mechanisms, e.g., gums. Slowly degenerating matrices may also be incorporated into the formulation.

Modified release oral formulations may be provided. Modified release may allow for specific release profiles.

Extended release oral formulations may be provided. Extended release may allow for release of active ingredient over a desired time period.

Additional discussions for varying release formulations and related terms may be found in Lesczek Krowczynski, *Extended-Release Dosage Forms,* 1987 (CRC Press, Inc.).

In certain aspects, the form of a controlled, modified or extended release oral formulation is a tablet, capsule, or microbeads for oral administration. In other aspects, controlled, modified or extended release formulations comprising suitable and effect treatment amounts of the desired components may be pills, powders, granules, sterile parenteral solutions or suspensions, oral solutions or suspensions, oil water emulsions as well as implants and microencapsulated delivery systems.

Other formulations may provide controlled, modified or extended release profiles. Compositions of the present invention may comprise conventional pharmaceutical binder, excipients and additives, which may act to control, modify or extend release when used in sufficient quantities. Coating agents, e.g., plasticizers, may be used to enhance the controlled, modified or extended release features of the compositions of the invention.

For oral formulations, the location of release may be the stomach, the small intestine (the duodenum, the jejunum, or the ileum), or the large intestine. The release can avoid the deleterious effects of the stomach environment, either by protection of the agent (or derivative) or by release of the agent (or derivative) beyond the stomach environment, such as in the intestine. To ensure full gastric resistance a coating temporally impermeable to at least pH 5.0 is useful. Examples of the more common inert ingredients that are used as enteric coatings are cellulose acetate trimellitate (CAT), hydroxypropylmethylcellulose phthalate (HPMCP), polyvinyl acetate phthalate (PVAP), poly(methacrylic acid-co-ethyl acrylate) 1:1, cellulose acetate phthalate (CAP), poly(methacylic acid-co-methyl methacrylate) 1:1, poly (methacylic acid-co-methyl methacrylate) 1:2, and natural shellac resin. These coatings may be used as mixed films.

i. Soft or Hard Gel Capsules

The methods utilize the oral administration of soft capsules containing nicotinamide riboside and pterostilbene or their equivalents. The soft capsule can be prepared using techniques well known in the art. For example, soft capsules are typically produced using a rotary die encapsulation process. Active agent formulations are fed into the encapsulation machine by gravity. In an embodiment, the formulation comprises pharmaceutical excipients such as olive oil, gelatin, glycerin, purified water, beeswax yellow, sunflower lecithin, silicon dioxide, titanium dioxide, F. D. & C Blue 1 and F. D. & C Red 4, microcrystalline cellulose, hypromellose, vegetable magnesium stearate, and/or silica.

A capsule shell can comprise one or more plasticizers such as glycerin, sorbitol, sorbitans, maltitol, glycerol, polyethylene glycol, polyalcohols with 3 to 6 carbon atoms, citric acid, citric acid esters, triethyl citrate and combinations thereof. In an embodiment, the plasticizer is glycerin.

In addition to the plasticizer(s), the capsule shell can include other suitable shell additives such as opacifiers, colorants, humectants, preservatives, flavorings, and buffering salts and acids.

Opacifiers are used to opacify the capsule shell when the encapsulated active agents are light sensitive. Suitable opacifiers include, but are not limited to, titanium dioxide, zinc oxide, calcium carbonate and combinations thereof. In an embodiment, the opacifier is titanium dioxide.

Colorants can be used to for marketing and product identification and/or differentiation purposes. Suitable colorants include synthetic and natural dyes and combinations thereof.

Humectants can be used to suppress the water activity of the softgel. Suitable humectants include glycerin and sorbitol, which are often components of the plasticizer composition. Due to the low water activity of dried, properly stored softgels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl (collectively known as "parabens") or combinations thereof.

One composition referred to as "BASIS®" includes nicotinamide riboside and pterostilbene as the active ingredients. This can be in a capsule formed of microcrystalline cellulose, hypromellose, vegetable magnesium stearate, olive oil, gelatin, glycerin, purified water, beeswax yellow, sunflower lecithin, silicon dioxide, titanium dioxide, F. D. & C Blue 1 and F. D. & C Red 4, or vegetarian hard capsules made solely of plant materials. Any embodiment may include microcrystalline cellulose, hypromellose, vegetable magnesium stearate, and/or silica.

Other pharmaceutical excipients that can be included in the disclosed formulations, include acetyl-L-carnitine, N-acetyl cysteine, α-lipoic acid, biotin, vitamin B6, vitamin B12, folic acid, resveratrol, vinpocetine, chromium picolinate, vitamin D3, naringin, quercetin, and creatine.

ii. Solutions and Suspensions

The methods can involve the use of composition which are administered as a liquid with an active agent dissolved (e.g., solution) or dispersed (e.g., suspension) in the composition. The solution or suspension may be prepared using one or more pharmaceutically acceptable excipients. Suitable excipients include, but are not limited to, surfactants, humectants, plasticizers, crystallization inhibitors, wetting agents, bulk filling agents, solubilizers, bioavailability enhancers, pH adjusting agents, flavorants and combinations iii. Controlled Delivery Polymeric Matrices Controlled release polymeric devices can be made for long term release systemically following implantation of a polymeric device (rod, cylinder, film, disk), injection or oral ingestion (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. The polymer may be cast as a thin slab or film, ranging from nanometers to four centimeters, a powder produced by grinding or other standard techniques, or even a gel such as a hydrogel.

Either non-biodegradable or biodegradable matrices can be used for delivery of disclosed compounds, although biodegradable matrices are present in certain embodiments. These may be natural or synthetic polymers, although synthetic polymers may be used in certain embodiments for characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release* 5:13-22 (1987); Mathiowitz, et al., *Reactive Polymers* 6:275-283 (1987); and Mathiowitz, et al., *J. Appl. Polymer Sci.* 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

C. Dosages and Dosage Regiments

Selection of a particular therapeutically effective dose can be determined (e.g., via clinical trials) by an ordinarily skilled artisan based upon the consideration of several factors which will be known to one of ordinary skill in the art. Such factors include the disease to be treated or prevented, the symptoms involved, the subject's body mass, the subject's immune status and other factors known by the skilled artisan. The precise dose to be employed in the formulation will also depend on the route of administration, and the seriousness of the disease-related wasting, and should be decided according to the judgment of the practitioner and each subject's circumstances. Effective doses can be extrapolated from dose-response curves derived from in vitro or animal model test systems.

The dose of the active compound to be administered to a subject, such as a human, is rather widely variable and can be subject to independent judgment. It is often practical to administer the daily dose of the active compound at various hours of the day. The amount of the active compound administered may depend on such factors as the solubility of the active component, the formulation used, subject condition (such as weight), and/or the route of administration.

The general range of a therapeutically effective amount of orally administered nicotinamide riboside or its equivalents, alone or in combination with pterostilbene or its equivalents, is in an amount of between about 50 mg and about 1500 mg, between about 100 mg and about 1500 mg, between about 100 mg and about 1000 mg per day, between about 125 mg and about 900 mg per day, between about 150 mg and about 850 mg per day, between about 200 mg to 700 mg per day, between about 200 mg to about 500 mg per day, about 250 mg per day, between about 1000 mg and about 1500 mg, or 250 mg per day.

The general range of a therapeutically effective amount of orally administered pterostilbene or its equivalents, alone or in combination with nicotinamide riboside or its equivalents, in an amount between about 25 mg and about 1000 mg, between about 100 mg and about 1000 mg, between about 25 mg and about 500 mg per day, between about 25 mg and about 250 mg per day, between about 30 mg and about 225 mg per day, between about 40 mg and about 200 mg per day, between about 45 mg and about 250 mg per day, about 50 mg per day, or 50 mg per day. In one embodiment, the compounds, compositions or pharmaceutical compositions containing nicotinamide riboside and pterostilbene are prepared as oral formulations.

In certain embodiments a composition may be administered in a dosage regimen over days, weeks, or months. Dosages may be multiple times per day or singular doses per day. Each dosage when dosages are administered over multiple days, weeks, or months may not be equal amounts. Dosage amounts during a dosage regimen may vary according to the amounts and ranges disclosed herein.

III. Methods of Use

Certain compositions and methods described herein may have beneficial effects on skin. Certain compositions and methods described herein may treat and/or prevent skin disorders. Certain compositions described herein may be oral compositions to provide oral formulations for treating and/or preventing skin disorders. Certain compositions and methods described herein may improve and/or maintain an aesthetic appearance of skin. In any embodiment, a composition may treat and/or prevent a skin disorder but may or may not treat rosacea, as indicated in the claims.

Skin disorders that are treated include, but are not limited to, those caused by sun exposure, inflammation, and autoimmune diseases. Skin disorders that are treated may or may not exclude rosacea, as indicated in the claims. Skin disorders that are treated may or may not include erythematotelangiectatic rosacea, telangiectasias, papulopustular rosacea and/or phymatous rosacea, as indicated in the claims.

i. Sun Exposure-Related Skin Disorders

Sun exposure-related skin disorders that are treated with the described compositions and methods include, but are not limited to, actinic keratoses, lentigines or age spots, seborrheic keratoses, sun burn, photosensitivity, moles, polymorphous light eruption, solar elastosis or wrinkles, skin cancer (such as melanoma, squamous cell carcinoma, basal cell carcinoma), and freckles.

ii. Inflammatory Skin Disorders

Inflammatory skin disorders that are treated with the described compositions and methods include, but are not limited to, psoriasis, contact dermatitis, atopic dermatitis, seborrheic dermatitis, asteatotic eczema, discoid eczema, hand eczema, gravitational/varicose eczema, eczematous drug eruptions, *lichen* simplex, acne, *lichen planus, pityriasis lichenoides*, keratosis *lichenoides* chronica, *lichen nitidus, lichen striatus*, mycosis fungoides, erythroderma, erythema multiforme, Stevens-Johnson Syndrome, vasculitis, and toxic epidermal necrolysis.

iii. Autoimmune Skin Disorders

Autoimmune skin disorders that are treated with the described compositions and methods include, but are not limited to, pyoderma gangrenosum, systemic lupus erythematosus, eosinophilic fasciitis, scleroderma, pemphigus vulgaris, bullous pemphigoid, alopecia areata, vitiligo, psoriasis, dermatomyositis, and dystrophic epidermolysis bullosa.

The present invention will be further understood by reference to the following non-limiting examples.

EXAMPLES

Example 1: Exemplary Composition

Materials: One composition is the product marketed by Elysium Health as "BASIS®".

TABLE 1

| Active Components of BASIS ® | |
|---|---|
| Component | Weight of component |
| Nicotinamide riboside | 250 mg |
| Pterostilbene | 50 mg |

BASIS® further contains the following pharmaceutical excipients: microcrystalline cellulose, hypromellose, vegetable magnesium stearate, olive oil, gelatin, glycerin, purified water, beeswax yellow, sunflower lecithin, silicon dioxide, titanium dioxide, F. D. & C Blue 1 and F. D. & C Red 4. Any embodiment may include microcrystalline cellulose, hypromellose, vegetable magnesium stearate, and/or silica.

Unless defined otherwise, all technical and scientific terms used herein have the same meanings as commonly understood by one of skill in the art to which the disclosed invention belongs. Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

We claim:

1. A method of treating sunburn in a patient in need thereof comprising orally administering a combination of a therapeutically effective amount of nicotinamide riboside and a therapeutically effective amount of pterostilbene, wherein the therapeutically effective amount of nicotinamide riboside is 250 mg per day, the therapeutically effective amount of pterostilbene is 50 mg per day.

2. The method of claim 1, wherein the therapeutically effective amount of nicotinamide riboside and the therapeutically effective amount of pterostilbene is administered in the same composition.

3. The method of claim 2, wherein the composition comprises a pharmaceutically acceptable excipient.

4. The method of claim 3, wherein the pharmaceutically acceptable excipient is selected from the group consisting of microcrystalline cellulose, hypromellose, vegetable magnesium stearate, olive oil, gelatin, glycerin, purified water, beeswax yellow, sunflower lecithin, silicon dioxide, titanium dioxide, F. D. & C Blue 1 and F. D. & C Red 4.

5. A method of treating lentigines or age spots in a patient in need thereof comprising orally administering a combination of a therapeutically effective amount of nicotinamide riboside and a therapeutically effective amount of pterostilbene, wherein the therapeutically effective amount of nicotinamide riboside is 250 mg per day, the therapeutically effective amount of pterostilbene is 50 mg per day.

6. A method of treating skin cancer in a patient in need thereof comprising orally administering a combination of a therapeutically effective amount of nicotinamide riboside and a therapeutically effective amount of pterostilbene, wherein the therapeutically effective amount of nicotinamide riboside is 250 mg per day, the therapeutically effective amount of pterostilbene is 50 mg per day.

* * * * *